United States Patent [19]
Yuen

[11] Patent Number: 4,984,564
[45] Date of Patent: Jan. 15, 1991

[54] SURGICAL RETRACTOR DEVICE

[76] Inventor: Frank Yuen, 110-20 71st Avenue, Forest Hills, N.Y. 11375

[21] Appl. No.: 413,266

[22] Filed: Sep. 27, 1989

[51] Int. Cl.$^5$ ............................................. A61B 17/02
[52] U.S. Cl. ........................................ 128/20; 128/3
[58] Field of Search ................................... 128/20, 3; 606/192-196

[56] References Cited

U.S. PATENT DOCUMENTS

| | | | |
|---|---|---|---|
| 2,812,758 | 11/1957 | Blumenschein | 128/20 |
| 3,030,947 | 4/1962 | Engelbert | 128/20 |
| 3,782,370 | 1/1974 | McDonald | 128/20 |
| 3,863,639 | 2/1975 | Kleaveland | 128/20 X |
| 4,501,264 | 2/1985 | Rockey | 606/192 |

FOREIGN PATENT DOCUMENTS 0797668  1/1981  U.S.S.R. .............................. 128/20

*Primary Examiner*—Benjamin Layno
*Attorney, Agent, or Firm*—Collard, Roe & Galgano

[57] ABSTRACT

The present invention relates to a surgical retractor which comprises an inflatable sleeve that may be deflated, when not in use, so as to assume a precoiled position; and which may be inflated by air pressure, when in use, so as to define an uncoiled generally circular aperture.

12 Claims, 1 Drawing Sheet

U.S. Patent  Jan. 15, 1991  4,984,564
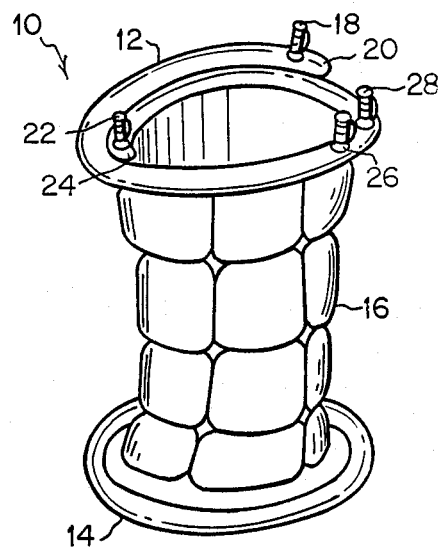
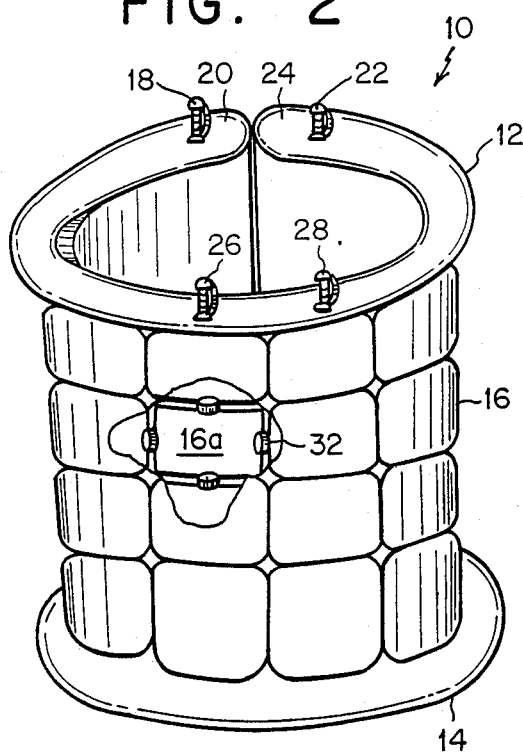
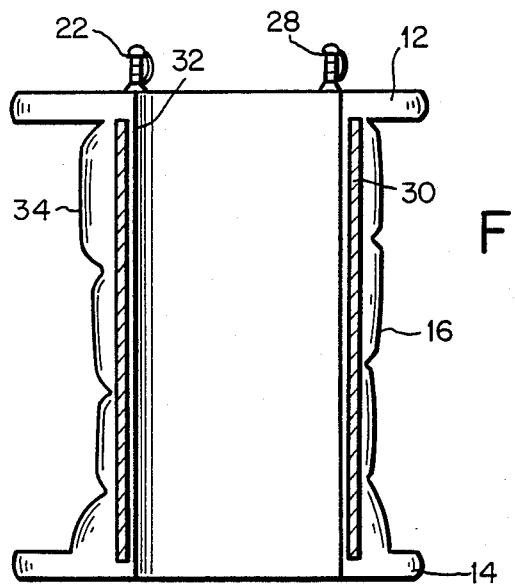
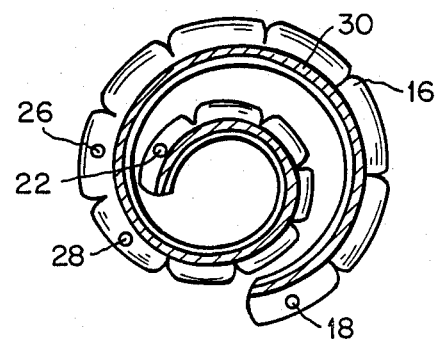
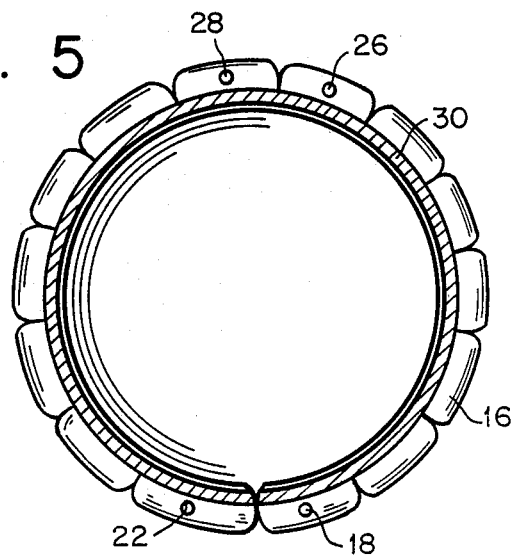

SURGICAL RETRACTOR DEVICE

BACKGROUND OF THE INVENTION

1. Field of the Invention

The present invention relates to a surgical retractor which comprises an inflatable sleeve that may be deflated, when not in use, so as to assume a precoiled position; and which may be inflated by air pressure, when in use, so as to assume an uncoiled state in which it defines a generally circular aperture.

2. The Prior Art

Surgical retractors are used for spreading apart or separating the walls of natural body orifices or for spreading the margins of surgical incisions. With the edges of an incision spread apart, the surgeon has access to the underlying tissues or organs permitting a clear view of the surgical site and access for a desired surgical or medical treatment. Thus, for example, an abdominal retractor may be used in an abdominal incision to hold back the skin, subcutaneous fat and the internal peritoneal wall for ready access to the many abdominal organs.

Examples of prior art surgical retractors and related medical devices are as follows.

U.S. Pat. No. 2,812,758 discloses a circular surgical retractor which can be expanded or contracted, apparently by hand, and then locked in position for producing a desired circular opening in the abdominal cavity.

U.S. Pat. Nos. 4,459,978 and 4,585,000 disclose expandable medical devices having fingers which can expand upon the retraction of a hub portion by the activation of a flexible shaft.

U.S. Pat. No. 3,807,393 discloses an expandable surgical retractor which again can be locked in expanded position after being manually extended.

U.S. Pat. No. 4,334,652 shows a circular expandable device which is, when contracted, used to clamp surgical bodies.

Each of these prior art devices have certain disadvantages. For example, during the retraction, or the clamping, it is difficult to observe or to reach the exposed anatomical structures. In addition, there is stressing and traumatizing of the tissue being retracted. These prior art problems are the result of having to hastily expand or contract the surgical retractor, whereby the forces being applied to the device and to the patient are not uniformly or smoothly employed, and the effect is to traumatize the tissue adjacent to the device. A further cause of tissue trauma/stress is the fact that direct, sustained contact between an unyielding retractor surface (a metal band, rim, fork or blade) and retracted tissue occurs. Another disadvantage is that a nurse or surgical attendant is required to be present for extended periods of time in order to manually maintain the retractor in position during a lengthy surgery.

OBJECTS OF THE INVENTION

It is an object of the present invention to provide a surgical retractor device that minimizes the trauma and stress of the tissue being retracted.

It is another object of the present invention to provide a fluid activated surgical retractor device that produces a circular surgical field based upon a precoiled expandable cylindrical sleeve.

These and other further objects of the present invention will become more apparent as the description thereof proceeds.

SUMMARY OF THE INVENTION

The present invention has the following advantages. The first is that in certain types of surgery, the present invention can provide a circular surgical field. This is superior to the diamond-shaped surgical field which is typically formed by applying opposing retraction on the cut surfaces of an incision along an axis perpendicular to the incision line. This diamond-shaped form of retraction has certain disadvantages in visualization of exposed anatomical structures as well as stressing and traumatizing the tissue being retracted.

The second advantage is that uniform pressure upon retracted tissue can be successfully applied if the surgical field is created by the gradual expansion of a precoiled sleeve or cuff against the tissue to be displaced. This is accomplished by inflating a cuff that has been affixed to the outer surface of the retractor wall. Inflation of the cuff has the tendency to straighten out the retractor. Since it is pre-coiled however, the retractor will desirably deform in the shape of an ever widening circle. The inflatable cuff provides conformity to the retracted tissue surfaces while it deforms as it expands the retractor.

A third advantage is that a compressed inert gas such as compressed air or nitrogen is used to uncoil and to expand the retractor device after the device is placed within the body cavity of the patient. By using a pressurized gas, it is not necessary to have a person in the operating room physically handling the retractor.

The present invention is directed to a surgical retractor device which comprises an inflatable sleeve that may be deflated, when not in use, so as to assume a precoiled position; and which may be inflated by air pressure, when in use, so as to assume an uncoiled state in which it defines a generally circular aperture.

The present invention is also directed to a surgical retractor device comprising a precoiled inflatable sleeve having a stationary end and a movable end;

a fluid inflow nozzle at said stationary end;

a fluid outflow nozzle at said movable end;

such that whenever a pressurized fluid is injected into said precoiled sleeve through said inflow nozzle, the movable end uncoils until the retractor device forms a circular aperture; and such that whenever said pressurized fluid is withdrawn from said uncoiled retractor device through said outflow nozzle, the movable end recoils until the retractor device becomes a precoiled sleeve.

BRIEF DESCRIPTION OF THE DRAWINGS

FIG. 1 shows a perspective view of a first embodiment of the surgical retractor device in a precoiled deflated state.

FIG. 2 shows a perspective view of the surgical retractor device in an uncoiled inflated state.

FIG. 3 shows a section view of a second embodiment of the surgical retractor of the invention.

FIG. 4 shows a top view of the surgical retractor of FIG. 3.

FIG. 5 shows a top view of the surgical retractor of FIG. 4 after it is uncoiled and expanded.

DESCRIPTION OF PREFERRED EMBODIMENTS

FIG. 1 shows a perspective view of a first embodiment of the surgical retractor 10 device in a precoiled deflated state. The surgical retractor device comprises a precoiled inflatable sleeve which has an upper lip 12, a lower lip 14, with an inflatable cuff or series of pockets 16 located between the upper lip and the lower lip.

There is a fluid inflow nozzle 18 located at the stationary end 20 of the device; and there is a fluid outflow nozzle 22 located at the movable end 24 of the device. Thus whenever a pressurized fluid, namely air, is injected into the precoiled sleeve through the inflow nozzle 18, the movable end 24 uncoils until the retractor device forms a circular aperture, as seen in FIG. 2. In addition, whenever the pressurized pneumatic fluid is withdrawn from the uncoiled retractor device through the outflow nozzle 22, the movable end 24 recoils until the retractor device becomes a precoiled sleeve once again, as shown in FIG. 1.

However, it is to be understood that there may only be one nozzle for both the inflow and the outflow of the fluid into and from the surgical retractor, and the location of this one nozzle is possible at anywhere along the upper lip 12. It is possible that both ends of the retractor may be movable.

The inflatable cuff 16 is made up of a multitude of individual pockets, as seen in FIG. 2 as 16a, which pockets are interconnected to one another through channel tube means 32. This provides a continuous fluid flow path between each and every one of the pockets. For the sake of clarity the interconnecting tubes 32 are only shown in place with regard to the one pocket 16a; however these tubes may be present between most of the cuff pockets or all of the cuff pockets.

The cuff pockets 16 are connected at their uppermost row to the lower edge of the upper lip and these pockets are connected along their lowermost row to the upper edge of the lower lip 14.

It may be desirable to have more than one inflow nozzle, and an example of a second inflow nozzle is nozzle 26. Likewise it may be desirable to have more than one outflow nozzle, and an example thereof is outflow nozzle 28.

FIG. 2 shows a perspective view of a first embodiment of the surgical retractor device 10 in an uncoiled and inflated state. The shape of the uncoiled retractor is cylindrical, as shown in FIG. 2. The purpose for having the retractor device cylindrical in shape is to provide the surgeon with a uniform field of vision over the area in which the operation will occur, and to minimize the trauma to the tissue being pushed aside as the retractor device is inflated by the fluid flowing into the device.

The surgical retractor of the invention may be composed of any thermoplastic, flexible, resilient material that can be initially sterilized before use. Examples of such plastics include polyethylene, polypropylene, copolymers thereof, as well as polyvinyl chloride polymers, or acrylic acid polymers and copolymers, that are inert to body fluids and medical liquids such as sterilants and cleaning liquids that may be present during the operation. The surgical retractor would be made by any of the known thermoplastic manufacturing techniques, such as blow molding.

The inflow and outflow nozzles are valves that may be provided with cap means in order to control the opening and closing of these valves. These valves may be integrally molded into the upper lip and be connected to the inflatable cuff pockets through the upper lip which will contain hollow sections in order to connect the nozzles with the inflatable cuff pockets.

FIG. 3 shows a section view of a second embodiment of the surgical retractor of the invention. In the embodiment in FIG. 1 there is no additional belt or ring 30 which is shown in FIG. 3. In other words, FIG. 3 represents a second embodiment of the present invention in which ring or belt 30 is located between the inner wall 32 and the outer wall 34 of cuff sleeve portion of the device.

FIG. 4 shows a top view of the surgical retractor of FIG. 3, showing the belt 30 coiled into a precoiled status. FIG. 5 shows a top view of the surgical retractor of FIG. 4, after it is uncoiled and expanded to be similar in appearance to the uncoiled retractor of FIG. 2. In FIG. 5, it can be seen that the belt 30 extends around the device.

The advantage of the second embodiment, which is shown in FIGS. 3, 4 and 5, is to prevent a wobbling by the retractor device along its longitudinal axis, because the belt provides a greater rigidity and stability, while also maintaining flexibility and resiliency in the device. In other words, the belt provides a uniform expansion or contraction of the device up and down along the longitudinal axis of the retractor device. This provides for a uniform field of vision for the surgeon, and this minimizes the trauma to the surrounding tissue of the patient. The upper and lower lip also serve to help provide a uniform expansion or contraction up and down the longitudinal axis while the retractor device is being used.

The surgical retractor device of the present invention would be utilized as follows. After the surgeon has made the necessary opening into the body cavity, the surgical retractor in its precoiled state is placed in the opening. Hoses connected to a source of pressurized air, or pressurized nitrogen gas, are connected to the inflow nozzle or nozzles. The air under pressure is slowly fed into the retractor device, so that it begins to expand by uncoiling in a systematic and controlled manner, until the degree of uncoiling is suitable for the surgeon's purposes. This could mean either a partial or a complete uncoiling of the surgical retractor device. Then the air flow is stopped and the pressure of the gas within the retractor device is maintained constantly, such that the opening within the device is constant. After the surgery is complete, and the surgeon no longer needs to have this device present within the patient, the amount of air pressure is reduced through the outflow nozzle in a controlled manner. This enables the device to begin to recoil itself by contracting and shrinking in diameter. After the device is completely deflated, it may be removed from the patient. The device can then be sterilized for further use, or it can be disposed of.

Other modifications will occur to those skilled in the art. For example it may be possible to use a saline solution to inflate the cuff, based upon a membrane that allows the osmotic transfer of a normal saline solution to penetrate through the surface membrane and to assist in bringing moisture to the exposed retracted tissue.

It may also be possible to use a metal, such as steel, as a construction material, if the device is to be considered for re-use. If a metal version is produced, it could be used with a disposable plastic cuff.

While the present invention has been described by reference to a few embodiments, it is to be understood that the present invention is not to be so limited; instead the invention is only to be defined by the scope of the following claims.

What is claimed is:

1. A surgical retractor device comprising an inflatable sleeve that is deflated, when not in use, so as to assume a precoiled position; and is inflated by air pressure, when in use, so as to assume an uncoiled state in which it defines a generally circular aperture.

2. The surgical retractor device of claim 1, further comprising one fluid inflow and outflow means for inflating and deflating said sleeve, respectively.

3. The surgical retractor device of claim 1, further comprising a belt located within and attached to said inflatable sleeve to strengthen said sleeve.

4. The surgical retractor device of claim 1, further comprising a belt which extends around the device.

5. A surgical retractor device comprising:
a precoiled inflatable sleeve having a stationary end and a movable end;
a fluid inflow nozzle at said stationary end;
a fluid outflow nozzle at said movable end;
such that whenever a pressurized fluid is injected into said precoiled sleeve through said inflow nozzle, the movable end uncoils until the retractor device defines a generally circular aperture; and
such that whenever said pressurized fluid is withdrawn from said uncoiled retractor device through said outflow nozzle, the movable end recoils until the retractor device becomes a precoiled sleeve.

6. The surgical retractor device of claim 5, comprising an upper lip at the top end of said device, in which said inflow nozzle and said outflow nozzle are located.

7. The surgical retractor device of claim 6, comprising a lower lip at the bottom end of said device.

8. The surgical retractor device of claim 7, comprising inflatable cuff pockets interconnected to one another to provide continuous fluid flow between each pocket and connected at the top end to the upper lip and connected at the bottom end to the lower lip.

9. The surgical retractor device of claim 5, further comprising a belt located within and attached to said inflatable sleeve to strengthen said sleeve.

10. A surgical retractor device comprising an inflatable sleeve that is deflated, when not in use, so as to assume a precoiled position; and is inflated by air pressure, when in use, so as to assume an uncoiled state in which it defines a generally circular aperture;
one fluid inflow and outflow means for inflating and deflating said sleeve, respectively; and
said device having two ends, both of which are movable to uncoil as the sleeve is inflated, and to recoil as the sleeve is deflated.

11. The surgical retractor device of claim 10, further comprising a belt located within and attached to said inflatable sleeve to strengthen said sleeve.

12. The surgical retractor device of claim 10, further comprising a belt which extends around the device.

* * * * *